United States Patent
Weinstein

(10) Patent No.: US 11,844,918 B2
(45) Date of Patent: Dec. 19, 2023

(54) APPARATUS FOR USE WITH A PRESSURE-REGULATING DEVICE

(71) Applicant: TRI.O MEDICAL DEVICE LTD, Maalot (IL)

(72) Inventor: Kfir Weinstein, Maalot (IL)

(73) Assignee: TRI.O MEDICAL DEVICE LTD, Maalot (IL)

( * ) Notice: Subject to any disclaimer, the term of this patent is extended or adjusted under 35 U.S.C. 154(b) by 0 days.

(21) Appl. No.: 17/239,637

(22) Filed: Apr. 25, 2021

(65) Prior Publication Data

US 2022/0339415 A1 Oct. 27, 2022

(51) Int. Cl.
*A61M 35/00* (2006.01)
*A61H 9/00* (2006.01)
*A61H 35/00* (2006.01)
*A61H 33/14* (2006.01)

(52) U.S. Cl.
CPC ............. *A61M 35/30* (2019.05); *A61H 9/005* (2013.01); *A61H 33/14* (2013.01); *A61H 35/00* (2013.01); *A61H 35/006* (2013.01)

(58) Field of Classification Search
CPC .......... A61H 9/00; A61H 9/005; A61H 9/007; A61H 9/0078; A61H 9/0085; A61H 9/0092; A61H 21/03; A61H 33/00; A61H 33/04; A61H 33/14; A61H 35/00; A61H 35/006; A61H 2201/01409; A61M 35/30; B60N 2/976; A61G 7/05769; A61G 7/05784; A63B 2225/62; A63B 71/081; F16J 3/041; F16J 3/02; F15B 15/103; F15B 15/10; A47C 21/044; A47G 9/0215; B32B 1/02; B32B 5/18; B32B 5/24; B32B 7/12; B32B 2307/724; Y10T 428/13; Y10T 428/1352; Y10T 428/1362; Y10T 428/1366;
(Continued)

(56) References Cited

U.S. PATENT DOCUMENTS 2,834,340 A * 5/1958 Walter ................ A61F 5/05816
128/DIG. 20
3,153,413 A * 10/1964 Gottfried ............ A61F 5/05816
601/149
(Continued)

FOREIGN PATENT DOCUMENTS

WO 2020126991 A1 6/2020

*Primary Examiner* — Justine R Yu
*Assistant Examiner* — Alexander Morales
(74) *Attorney, Agent, or Firm* — Momentum IP; Marc Van Dyke

(57) ABSTRACT

An apparatus for use in applying a therapy to a human limb includes a bag for surrounding all or part of the limb. The apparatus also includes a connection arrangement, mounted to a wall of the bag in a distal portion of the bag, that enables therethrough a flow of a gas between a pressure-regulating device and an interior space of the bag. The apparatus also includes a gas-permeable strip affixed to an interior surface of the bag and having a length equal to at least 70% of the bag's length. The distal end of the strip is in communication with the connection arrangement in the distal portion of the bag, and a proximal end of the strip is disposed in a proximal portion of the bag. The strip contains a partially compressible, gas-permeable material forming a lengthwise gas-flow pathway.

15 Claims, 10 Drawing Sheets

(58) Field of Classification Search
CPC ....... Y10T 428/1376; A61F 2007/0091; A61F 5/05816; A61F 5/05833
USPC .......................................... 92/91–92; 601/6–7
See application file for complete search history.

(56) References Cited

U.S. PATENT DOCUMENTS

| | | | | |
|---|---|---|---|---|
| 3,811,434 A * | 5/1974 | Jacobson | ............ | A61F 5/05816 128/DIG. 20 |
| 5,029,579 A * | 7/1991 | Trammell | ............ | A61H 9/0071 128/205.26 |
| 5,535,888 A * | 7/1996 | De Luca | ............ | B65D 81/3893 206/521 |
| 9,724,267 B2 * | 8/2017 | Wyss | ................ | A61M 5/14244 |
| 10,245,207 B2 | 4/2019 | Avni | | |
| 2005/0070828 A1 * | 3/2005 | Hampson | ............ | A61H 9/0092 601/152 |
| 2006/0241535 A1 * | 10/2006 | Chan | .................... | A61H 35/00 601/16 |
| 2008/0208088 A1 * | 8/2008 | Cazzini | ................ | A61M 1/917 602/13 |
| 2009/0062703 A1 * | 3/2009 | Meyer | ................. | A61H 9/0078 602/13 |
| 2009/0124987 A1 * | 5/2009 | Eriksson | ................ | A61B 90/40 604/304 |
| 2009/0270910 A1 * | 10/2009 | Hargens | ................ | A61H 9/005 606/201 |
| 2010/0042027 A1 * | 2/2010 | Hirata | ................ | A61F 5/05816 601/151 |
| 2010/0150991 A1 | 6/2010 | Bernstein | | |
| 2011/0288458 A1 * | 11/2011 | Jones | .................... | A61H 9/0078 601/149 |
| 2013/0053735 A1 * | 2/2013 | Branch | ................ | A61H 1/0277 601/5 |
| 2013/0072836 A1 * | 3/2013 | Heaton | ............. | A61H 23/0263 601/152 |
| 2013/0165821 A1 * | 6/2013 | Freedman | ........... | A61F 13/0279 601/2 |
| 2013/0192610 A1 * | 8/2013 | Gagnon | ............. | A61G 10/00 604/23 |
| 2014/0276288 A1 * | 9/2014 | Randolph | ............ | A61H 9/0057 601/152 |
| 2015/0094628 A1 * | 4/2015 | Crowley | .................. | A61H 9/00 601/148 |
| 2015/0190286 A1 * | 7/2015 | Allen | ................... | A61F 13/0216 604/319 |
| 2015/0224015 A1 * | 8/2015 | Wilford | ............... | A61H 9/0092 601/151 |
| 2019/0083194 A1 * | 3/2019 | Teunissen | ............. | A61B 46/20 |
| 2019/0307601 A1 * | 10/2019 | Hittman | ............. | A41D 13/0053 |
| 2020/0113773 A1 * | 4/2020 | Ramanan | ............ | A61H 9/0092 |
| 2020/0121510 A1 * | 4/2020 | Hartwell | ............ | A61F 13/0206 |
| 2021/0137774 A1 * | 5/2021 | Quan | ................. | A61F 13/0216 604/319 |

\* cited by examiner

TOP VIEW

VIEW A-A FROM FIG. 4A

VIEW A-A FROM FIG. 4A

VIEW A-A FROM FIG. 4A

VIEW A-A FROM FIG. 4A

VIEW A-A FROM FIG. 4A

APPARATUS FOR USE WITH A PRESSURE-REGULATING DEVICE

FIELD OF THE INVENTION

The present invention relates to articles of manufacture comprising apparatuses for use in gas and pressure therapies applied to human limbs and torsos, and particularly to apparatuses intended to be used in conjunction with pressure-regulating devices.

BACKGROUND

Pressure-regulating devices have been utilized in a variety of therapies. In many cases, therapies are applied by improvising pressure-retaining volumes above and around a wound or section of a limb or torso. In some cases, internal 'gas-bridges' between connection arrangements in the improvised volumes and the wound itself are also improvised, for example by cutting up pieces of an open-cell foam to create gas pathways within the volume. Thus, practices disclosed to date are imprecise, ad hoc, and difficult to maintain in sterile conditions. Further, the improvised pressure-retaining volumes are not appropriate for combination with other gas therapies or with other pressure therapies. Therefore, there is a need for ready-to-use apparatuses that can be used in a variety of therapies employing pressure-regulating devices and/or various gases.

SUMMARY

Embodiments of the present invention relate to apparatuses for use with a pressure-regulating device, in applying a therapy to a human limb. According to embodiments, there is provided an apparatus for use, with a pressure-regulating device, in applying a therapy to a human limb, comprises: (a) a bag formed to receive, in a donned mode, at least a portion of the limb, through an opening in a proximal portion of the bag; (b) a multilayer strip comprising a bottommost layer affixed to an interior surface of the bag, wherein a distal end of said multilayer strip is disposed in a distal portion of the bag, and wherein a proximal end of said multilayer strip is disposed in said proximal portion of the bag; and (c) a connection arrangement mounted to a wall of the bag in said distal portion thereof, the connection arrangement being effective, in a pressure-regulating mode, to enable therethrough a flow of a gas between the pressure-regulating device and an interior space of the bag, said multilayer strip further comprising an upper layer comprising a partially compressible material defining a gas-flow pathway disposed lengthwise within the bag, between said connection arrangement and said proximal portion of the bag.

In some embodiments, said lengthwise gas-flow pathway can be maintained when a gas pressure in the bag is at most 660 mm Hg. In some embodiments, said lengthwise gas-flow pathway can be maintained when a gas pressure inside the bag is 560 mm Hg.

In some embodiments, said multilayer strip can have a thickness:width dimensionless aspect ratio of between 1:2.5 and 1:20.

In some embodiments, said lengthwise gas-flow pathway can be maintained when a mechanical pressure of 20 mm Hg gauge is applied externally to the bag and transmitted through a wall of the bag to an uppermost layer of the multilayer strip. In some embodiments, said lengthwise gas-flow pathway can be maintained when a mechanical pressure of 60 mm Hg gauge is applied externally to the bag and transmitted through a wall of the bag to an uppermost layer of the multilayer strip.

In some embodiments, said multilayer strip can have a Shore A hardness of at most 70, or at most 60, or at most 50, or at most 40.

In some embodiments, it can be that said distal end of said multilayer strip is in fluid communication with said connection arrangement such that said partially compressible material forms a gas-flow pathway from said connection arrangement to said proximal end of said multilayer strip.

In some embodiments, said multilayer strip can have a length-to-width ratio of at least 3:1, or of at least 5:1, or at least 10:1. In some embodiments, said multilayer strip can have a length of at least 10 cm, or at least 15 cm, or at least 20 cm, or at least 25 cm, or at least 30 cm. In some embodiments, said multilayer strip can have a thickness of no more than 3.5 mm, or no more than 5 mm, or no more than 7.5 mm, or no more than 10 mm. In some embodiments, said upper layer can have a thickness of no more than 3.5 mm, or no more than 5 mm, or no more than 7.5 mm, or no more than 10 mm.

In some embodiments, the bag can be sized to receive a hand or a foot. In some embodiments, the bag can be sized to receive, lengthwise, at least a majority of an adult human arm. In some embodiments, the bag can be sized to receive, lengthwise, at least a majority of an adult human leg.

In some embodiments, said multilayer strip can have a length equal to at least 20% of a length of the bag.

In some embodiments, said multilayer strip can have a length equal to at least 30% of a length of the bag.

In some embodiments, said multilayer strip can have a length equal to at least 40% of a length of the bag.

In some embodiments, said multilayer strip can have a length equal to at least 50% of a length of the bag.

In some embodiments, said multilayer strip can have a length equal to at least 60% of a length of the bag.

In some embodiments, said multilayer strip can have a length equal to at least 70% of a length of the bag.

In some embodiments, it can be that (i) said distal portion of the bag includes a distally-disposed tab section open to said interior space of the bag, said distal tab section having a width less than 25% of a maximum width of said distal portion of the bag, and/or (ii) said connection arrangement is mounted at least partly within said distally-disposed tab section.

In some embodiments, the therapy can include a negative-pressure wound therapy. In some embodiments, said pressure-regulating mode can include an interior of the bag being under a vacuum. In some embodiments, said pressure-regulating mode can include an absolute pressure inside the bag within a range of 460 mm Hg to 1060 mm Hg, or within a range of 560 mm Hg to 960 mm Hg, or within a range of 460 mm Hg to 760 mm Hg, or within a range of 560 mm Hg to 760 hg, or within a range of 760 mm Hg to 1060 mm Hg, or within a range of 760 mm Hg to 960 mm Hg, or within a range of 760 mm Hg to 850 mm Hg.

In some embodiments, said pressure-regulating mode can include a pressure applied externally to the bag and transmitted through a wall of the bag to an uppermost layer of the multilayer strip, said externally-applied pressure being over a range of 0 mm Hg to 30 mm Hg. In some embodiments, said pressure-regulating mode can includes a pressure applied externally to the bag and transmitted through a wall of the bag to an uppermost layer of the multilayer strip, said externally-applied pressure being over a range of 0 mm Hg to 80 mm Hg.

In some embodiments, said multilayer strip can have a thickness:width dimensionless aspect ratio of between 1:1.5 and 1:20, or between 1:2.5 and 1:15, or between 1:5 and 1:15, or between 1:8 and 1:12.

In some embodiments, said bottommost layer can include an adhesive. In some embodiments, said multilayer strip can be attached to a first wall of the bag and the connection arrangement is mounted to a second wall of the bag.

In some embodiments, said multilayer strip can be effective to maintain fluid communication along a lengthwise path when a portion of said path is subjected to an externally-applied positive pressure at 100 mm Hg.

According to embodiments of the invention, an apparatus for use, with a pressure-regulating device, in applying a therapy to a human limb comprises: (a) a bag formed to surround, in a donned mode, at least a portion of the limb; (b) a connection arrangement mounted to a wall of the bag in a distal portion of the bag, the connection arrangement being effective to enable therethrough a flow of a gas between the pressure-regulating device and an interior space of the bag in a pressure-regulating mode; and (c) a gas-permeable strip affixed to an interior surface of the bag and having a length equal to at least 70% of a length of the bag, a distal end of said gas-permeable strip being in communication with said connection arrangement in said distal portion of the bag, and a proximal end of said gas-permeable strip being disposed in a proximal portion of the bag, said gas-permeable strip comprising a partially compressible, gas-permeable material forming a lengthwise gas-flow pathway.

According to embodiments of the invention, a kit can comprise (i) the apparatus according to any of the embodiments disclosed hereinabove, and/or (ii) an elastic ribbon of a gas-pathway material for disposition, in an on-limb configuration, as a transverse extension of the gas-flow pathway around the limb. In some embodiments, the kit can additionally comprise a sponge for mediating between said partially compressible material and a wound. In some embodiments, the kit can additionally (or alternatively) comprise a limb-sealing tape.

According to embodiments of the invention, an apparatus for use, with a pressure-regulating device, in applying a therapy to a human limb, comprises: (a) a bag formed to surround, in a donned mode, at least a portion of the limb; (b) a connection arrangement mounted to a wall of the bag in a distal portion of the bag, the connection arrangement being effective to enable therethrough a flow of a gas between the pressure-regulating device and an interior space of the bag in a pressure-regulating mode; and (c) a gas-permeable strip affixed to an interior surface of the bag, a distal end of said gas-permeable strip being in communication with said connection arrangement in said distal portion of the bag, and a proximal end of said gas-permeable strip being disposed in a proximal portion of the bag, said gas-permeable strip comprising a partially compressible, gas-permeable material forming a lengthwise gas-flow pathway, wherein said gas-permeable strip has a thickness:width dimensionless aspect ratio of between 1:5 and 1:15.

In some embodiments, the strip or multi-layer strip forms a lengthwise gas-flow pathway at least in said pressure-regulating mode.

In some embodiments, said strip or multilayer strip can have a length equal to at least 40% of a length of the bag, a thickness:width dimensionless aspect ratio of between 1:1.5 and 1:20, and a length-to-width ratio of at least 3:1.

In some embodiments, said strip or multilayer strip can have a length equal to at least 50% of a length of the bag, a thickness:width dimensionless aspect ratio of between 1:2.5 and 1:20, and a length-to-width ratio of at least 5:1.

In some embodiments, said strip or multilayer strip can have a length equal to at least 40% of a length of the bag, a thickness:width dimensionless aspect ratio of between 1:2.5 and 1:20, and a length-to-width ratio of at least 3:1, and said strip or multilayer strip comprises a partially compressible, gas-permeable material that forms a lengthwise gas-flow pathway (at least) in a pressure-regulating mode over an absolute pressure range within the bag of 560 mm Hg to 960 mm Hg.

In some embodiments, said strip or multilayer strip can have a length equal to at least 60% of a length of the bag, a thickness:width dimensionless aspect ratio of between 1:2.5 and 1:20, and a length-to-width ratio of at least 3:1, and said strip or multilayer strip comprises a partially compressible, gas-permeable material that forms a lengthwise gas-flow pathway (at least) in a pressure-regulating mode over an absolute pressure range within the bag of 560 mm Hg to 960 mm Hg, and said strip or multilayer strip comprises a partially compressible, gas-permeable material that forms a lengthwise gas-flow pathway (at least) in a pressure-regulating mode that includes an externally applied pressure over a gauge pressure range of 0 mm Hg to 30 mm Hg.

BRIEF DESCRIPTION OF THE DRAWINGS

The invention will now be described further, by way of example, with reference to the accompanying drawings, in which the dimensions of components and features shown in the figures are chosen for convenience and clarity of presentation and not necessarily to scale. In the drawings.

DETAILED DESCRIPTION OF THE ILLUSTRATED EMBODIMENTS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are generally used to designate like elements. Subscripted reference numbers (e.g., $10_1$) or letter-modified reference numbers (e.g., $100_A$) are used to designate multiple separate appearances of elements in a single drawing, e.g. $10_1$ is a single appearance (out of a plurality of appearances) of element 10, and $100_A$ is a single appearance (out of a plurality of appearances) of element 100.

Embodiments of the invention include apparatuses for use in pressure-related therapies applied to a human user's body, and in particular (although not exclusively) to one or more of the user's limbs. The apparatus is for use with a pressure-relating device, which can increase, decrease, and/or maintain a gas pressure within a bag component of the apparatus, and/or replace a gas within the bag. The bag is configured to surround a user's limb so that other components of the apparatus are disposed to form a gas-flow pathway to a treatment area, the pathway being viable even when the pressure in the bag is reduced.

Figure 1:
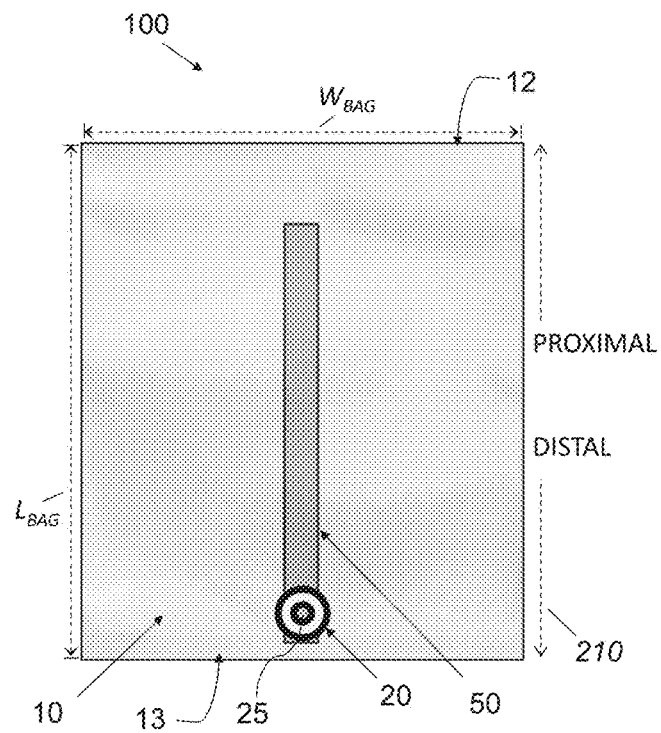
FIGS. 1 and 2 are schematic illustrations of exemplary apparatuses according to embodiments of the present invention.

We now refer to the figures and in particular to FIG. 1, which schematically illustrates, in a non-limiting example, an apparatus 100 for use in a therapy. The apparatus includes a pliable bag 10, shown in FIG. 1 in a two-dimensional projection, or in an initial before-use mode and in an unconnected state.

For simplicity, bags are characterized throughout this disclosure as having two opposing walls; however, some bags according to embodiments can be produced to have a single 'endless' wall, e.g., a continuous sheet of polymer that can be closed or sealed at one end and open at the other end. Nonetheless, when flattened, such a bag has two opposing walls. Bags as disclosed herein can be either seamed or seamless. Bags (and/or apparatuses comprising bags) can be provided in a continuous roll; alternatively or additionally, bags (and/or apparatus comprising bags) can be provided in an initial (pre-use) mode having two sealed ends, wherein a first end is designated for opening to initiate use. In some designs, a bag can be openable simply by separating two opposing walls. In some other designs, a user may have to perform an additional action, such as, for example, tearing off a sealing strip at the top of the bag. All of these variants in the bag design are within the scope of the invention. In addition, for simplicity, all illustrations of bags in the accompanying figures are of rectangular bags, but the embodiments can be implemented with bags of any shape that is suitable for the application, as will be appreciated by those of skill in the art. For example, a bag for an apparatus intended to be used with a patients hand might be oval (in a two-dimensional projection), or have rounded corners.

Bags according to the embodiments are produced from any suitably pliable material that can maintain a positive and/or negative pressure over a limited period of time, i.e., minutes or hours, but not necessarily days or weeks. Suitable construction materials for bags having low permeability and high pliability include polymers such as various grades of polyethylene, polypropylene and polyvinyl chloride. Low permeability to molecules such as $N_2$, $CO_2$, $O_2$ and $O_3$ can be a desirable characteristic in order to substantially isolate the interior of the bag, once sealed against a limb in a donned mode, from the surrounding atmosphere for the duration of a therapy session or a portion thereof. A construction material can be selected for compatibility with ozone gas, such as, for example, a polyethylene. Maintaining the pressure is generally a function of permeability of the construction material(s) of the bag, and in some cases thickness of the material. "Maintaining" a pressure, as the term is used herein should be understood to mean maintaining a set or specified pressure, or within 0.1% of the set or specified pressure over the course of a minute, or within 0.5%, or within 1%, or within 2%, or within 3%, or within 4%, or within 5% over the course of a minute. Maintaining can also include making small adjustments, e.g., by a pressure-regulating device connected to the bag, in order to reduce the variation in pressure. "Positive" and "negative" pressures should be understood to mean that a pressure is respectively higher or lower than ambient pressure. For example, if ambient pressure is 760 mm Hg (millimeters of mercury), then 460 mm Hg would be called a negative pressure and 1,060 mm Hg would be called a positive pressure. Thus, a negative-pressure therapy is a therapy applied at a pressure below ambient pressure; a negative pressure, i.e., a pressure greater than 0 mm Hg and less than ambient pressure can also be characterized herein as being "a partial vacuum" or similar.

The apparatus 100 of FIG. 1 additionally comprises a strip 50 and a connection arrangement 20. The bag 10 of FIG. 1, like all other bags 10 in the accompanying figures, is shown as at least partly 'transparent' so that strip 50 is 'visible' within. Although there may be operational advantages to the bag 10 being at least partly transparent, or at least translucent, it is not required in the embodiments disclosed herein. Thus, in some examples, the bag 10 is opaque. The strip 50, in some embodiments, is a multi-layer strip, i.e., a strip comprising two or more layers, as will be discussed below in connection with FIGS. 4B-E. In some embodiments, the strip 50 is a gas-permeable strip comprising one or more layers, as will be discussed below in connection with FIGS. 4D and 4F. The strip 50 is affixed to an interior surface of the bag 10, i.e., a bag-surface in direct fluid communication with the interior volume of the bag. In embodiments, the affixing includes applying an adhesive so that the strip 50 is bonded, e.g., glued, to the interior surface of the bag 10. In some embodiments, the affixing is by a heat-based process such as, in a non-limiting example, heat welding, such that the strip 50 is heat-welded to the interior surface of the bag 10.

The connection arrangement 20 is for connecting thereto a gas-connection hose introduced to mediate between a pressure-regulating device and the bag. The connection arrangement includes an opening 25 that allows a flow of gas, e.g., in the case of an increase or decrease in pressure, between the pressure-regulating device and the interior of the bag. In other words, pressure within the bag is regulated by connecting the pressure-regulating device to the connection arrangement 20. In some examples, the connection arrangement opening 25 is a simple hole, and in other examples the opening 25 includes one side of a male-female connection arrangement, or any other type of connection arrangement that matches a gas-connection hose suitable for use with the pressure-regulating device.

Respective "distal" and "proximal" directions of are indicated in FIG. 1 by arrow 210. The proximal end 12 of a bag 10 is that portion or end through which a user's limb can be inserted, and the distal end 13 is the opposite end. The connection arrangement 20 is mounted to a wall of the bag 10 in a distal portion, or close to the distal end 13. The strip 50 has a distal end in direct fluid communication with the connection arrangement 20 (including, specifically, the opening 25), and a proximal end disposed in a proximal portion of the bag 10. The proximal portion of the bag makes up as much as 50% of the bag 10, or as much as 40%, or as much as 30%, or as much as 25%, or as much as 20%, or even less. Thus, in some embodiments, the length of the strip 50 (its longer dimension, labeled $L_{STRIP}$ in FIG. 4A) is equal to at least 50% of the length of the bag 10, or at least 60%, or at least 70%, or at least 75%, or at least 80%, or at least 85%, or at least 90%, or at least 95%. The length of the bag 10 is indicated in FIG. 1 as $L_{BAG}$. The length $L_{BAG}$ can be the largest dimension of the bag 10 as shown in FIG. 1, but this may not be the case in every implementation. Therefore, the length $L_{BAG}$ can be considered to be a distance from the proximal end 12 to the distal end 13 of the bag 10.

Figure 2:
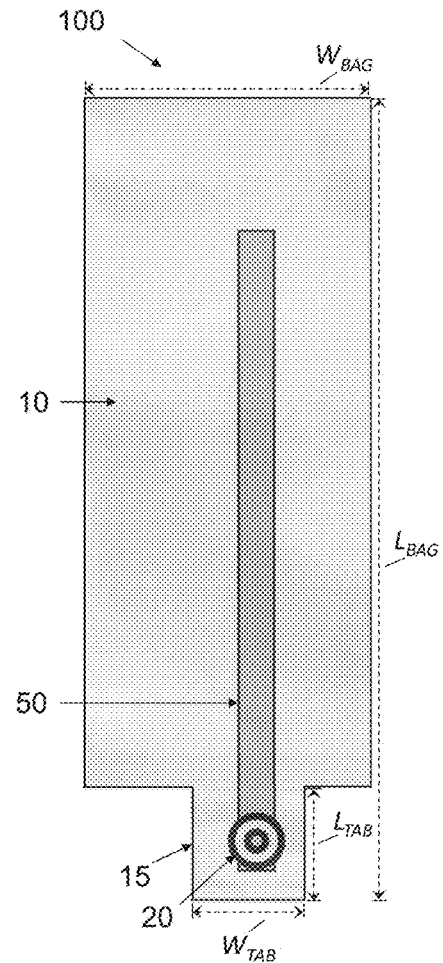

In embodiments, it can be desirable to 'distance' the connection arrangement 20 so it does not come into contact with the user's limb, e.g., to possibly cause discomfort. FIG. 2 shows a non-limiting example of an apparatus 100 comprising a bag 10 having a distal extension in the form of a tab 15. The tab 15 is open to the interior volume of the rest of the bag 10. In the example of FIG. 2, the connection arrangement 20 is mounted to an interior wall of the bag within the tab section 15, such that there is less opportunity for a user's limb to come into direct contact with the connection arrangement 20. In order for the use of a tab section 15 to be particularly effective in preventing direct contact with a user's limb, it is preferably of a narrower width than the rest of the bag 10: for example, the width of the tab section 15, indicated in FIG. 2 as $W_{TAB}$ is limited to being less than 30% of the width of the bag 10 ($W_{BAG}$) In some embodiments, $W_{TAB}$ is less than 25% of $W_{BAG}$, or less than 20%, or less than 15%, or less than 10%. In some embodiments, the length of the tab 15, indicated in FIG. 2 as $L_{TAB}$, is less than 25% of $L_{BAG}$, which is the total length of the bag 10, including the tab section 15, as shown in FIG. 2.

Figure 3:
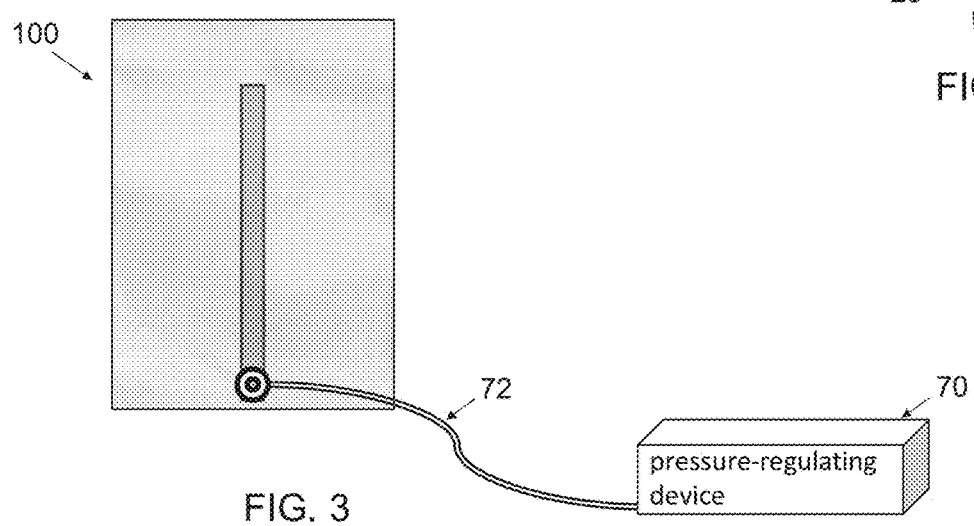
FIG. 3 is a schematic illustration of an apparatus connected, via a gas connection hose, to a pressure-regulating device, according to embodiments of the present invention.

FIG. 3 shows an apparatus 100 directly connected to a pressure-regulating device 70 by a gas-connector hose 72. In some embodiments, the connection is not a direct connection. In some embodiments, the hose 72 can include gas-switching capabilities and/or multiple input/output connections. In some embodiments, the hose 72 is part of, or permanently attached to the pressure-regulating device 70, and in other embodiments is a separate element. The pressure-regulating device 70 can be any device suitable for applying and/or maintaining a pressure higher or lower than ambient pressure, e.g., for applying a therapy to a user's limb or torso. Examples of suitable pressure-regulating devices include, and not exhaustively: a negative-pressure therapy unit, an ozone therapy unit, a sequential pressure therapy unit, and a unit combining two or more of the therapies.

We now refer to FIGS. 4A-F.

Figure 4A:
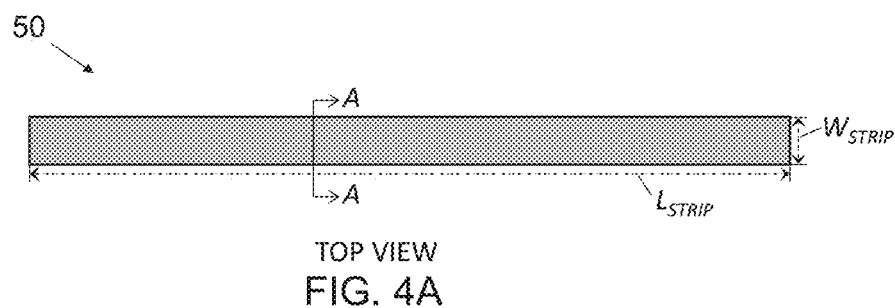
FIG. 4A is a schematic top view of a strip, according to embodiments of the present invention.

FIG. 4A is a top view of a strip 50 according to embodiments. The strip 50 has a length $L_{STRIP}$ and a width $W_{STRIP}$. In embodiments, the length $L_{STRIP}$ is at least 3 times longer than width $W_{STRIP}$, or at least 5 times longer, or at least 10 times longer. In some embodiments, a ration of $L_{STRIP}$:$W_{STRIP}$ is between 3:1 and 5:1, or between 3:1 and 10:1, or between 3:1 and 20:1, or between 3:1 and 30:1, or between 5:1 and 10:1, or between 5:1 and 20:1, or between 5:1 and 30:1, or between 10:1 and 20:1, or between 10:1 and 30:1, or between 20:1 and 30:1.

In embodiments, the length $L_{STRIP}$ is at least 10 cm, or at least 15 cm, or at least 20 cm, or at least 25 cm, or at least 30 cm. In embodiments, the width $W_{STRIP}$ is between 1 cm and 6 cm, or between 2 cm and 5 cm, or between 2.5 cm and 4.5 cm. In some embodiments, the width $W_{STRIP}$ is between 1 cm and 2 cm, or between 1 cm and 3 cm, or between 1 cm and 4 cm, or between 1 cm and 5 cm, or between 2 cm and 3 cm, or between 2 cm and 4 cm, or between 2 cm and 5 cm, or between 2 cm and 6 cm, or between 3 cm and 4 cm, or between 3 cm and 5 cm, or between 3 cm and 6 cm, or between 4 cm and 5 cm, or between 4 cm and 6 cm, or between 5 cm and 6 cm. All ranges cited throughout this specification are inclusive.

Figure 4B:
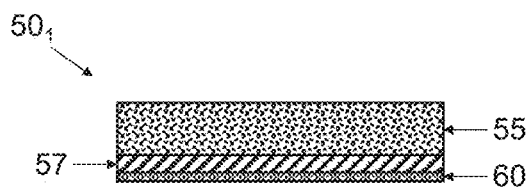
FIGS. 4B, 4C, 4D, 4E, and 4F are schematic transverse cross-sectional views of strips, according to embodiments of the present invention.
Figure 4C:
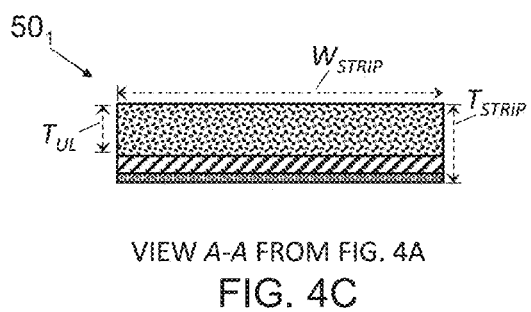
Figure 4D:
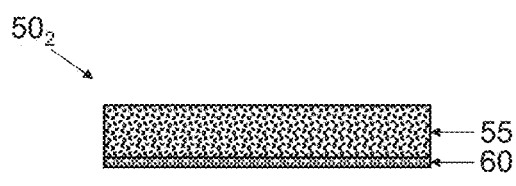
Figure 4E:
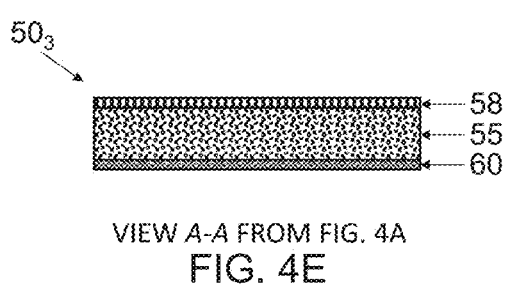
Figure 4F:

FIGS. 4B-F are schematic illustrations of respective transverse cross-sections of various strips 50 according to embodiments, each of the respective illustrations corresponding to view A-A in FIG. 4A. FIG. 4B shows strip $50_1$ comprising a bottommost layer 60, an intermediate layer 57 and an upper layer 55 comprising a partially-compressible gas-permeable material. In an example, the bottommost layer 60 is an adhesive layer. In another example, the bottommost layer 60 comprises a fabric that can be affixed to a wall of a bag by heat, for example by heat-welding. In an example, the intermediate layer 57 comprises a tightly woven or nonwoven fabric, and the upper layer 55 comprises one of a loosely woven fabric, a loop fabric, and a felt. As shown in FIG. 4C, the upper layer 55 has a thickness $T_{UL}$, and the strip 50 has a total thickness of $T_{STRIP}$. In some embodiments, the strip 50 has a total thickness $T_{STRIP}$ no more than 3.5 mm, or no more than 5 mm, or no more than 7.5 mm, or no more than 10 mm. In some embodiments, the upper layer 55 has a thickness of no more than 3.5 mm, or no more than 5 mm, or no more than 7.5 mm, or no more than 10 mm. In embodiments, it can be desirable for the strip 50 to be rather 'soft' so as not to cause undue discomfort to a user should the user's limb, for example, rest on part of the strip 50. In some embodiments, the strip 50 has a Shore A hardness of at most 70, or at most 60, or at most 50, or at most 40. In some embodiments, the gas-permeable upper layer 55 has a Shore A hardness of at most 70, or at most 60, or at most 50, or at most 40.

A strip 50 is characterized by a dimensionless aspect ratio of $T_{STRIP}/W_{STRIP}$. In embodiments, $T_{STRIP}/W_{STRIP}$ is between 1:1.5 and 1:20, or between 1:5 and 1:15, or between 1:8 and 1:12. In some embodiments, $T_{STRIP}/W_{STRIP}$ is between 1:1.5 and 1:5, or between 1:1.5 and 1:10, or between 1:1.5 and 1:15, or between 1:1.5 and 1:20, or between 1:1.5 and 1:30, or between 1:5 and 1:10, or between 1:5 and 1:12, or between 1:5 and 1:20, or between 1:1.5 and 1:30, or between 1:8 and 1:15, or between 1:8 and 1:20, or between 1:8 and 1:30, or between 1:10 and 1:15, or between 1:10 and 1:20, or between 1:10 and 1:30, or between 1:12 and 1:20, or between 1:12 and 1:30, or between 1:15 and 1:20, or between 1:15 and 1:30, or between 1:20 and 1:30.

An upper layer 55 is characterized by a dimensionless aspect ratio of $T_{UL}/W_{STRIP}$. In embodiments, $T_{UL}/W_{STRIP}$ is between 1:1.5 and 1:20, or between 1:5 and 1:15, or between 1:8 and 1:12. In some embodiments, $T_{UL}/W_{STRIP}$ is between 1:1.5 and 1:5, or between 1:1.5 and 1:10, or between 1:1.5 and 1:15, or between 1:1.5 and 1:20, or between 1:1.5 and 1:30, or between 1:5 and 1:10, or between 1:5 and 1:12, or between 1:5 and 1:20, or between 1:1.5 and 1:30, or between 1:8 and 1:15, or between 1:8 and 1:20, or between 1:8 and 1:30, or between 1:10 and 1:15, or between 1:10 and 1:20, or between 1:10 and 1:30, or between 1:12 and 1:20, or between 1:12 and 1:30, or between 1:15 and 1:20, or between 1:15 and 1:30, or between 1:20 and 1:30.

The strip $50_2$ of FIG. 4D comprises a partly-compressible upper layer 55 and a bottommost layer 60 as previously described. The strip $50_3$ of FIG. 4E comprises the partly-compressible upper layer 55 and the bottommost layer 60, and an uppermost layer 58, such as, for example, a coating applied to the upper layer 55. The strip $50_4$ of FIG. 4F comprises a partly-compressible, gas-permeable layer 55, which, in embodiments, is affixed to a wall of a bag, e.g., with an adhesive or by heat.

Figure 5A:
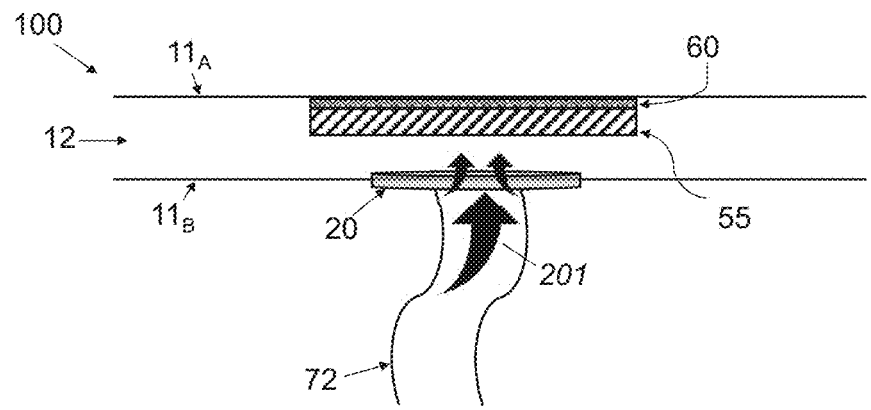
FIGS. 5A and 5B are schematic illustrations showing components of an apparatus according to embodiments of the present invention, including a connection arrangement with a gas connection hose connected thereto, two opposing walls of a bag, and a strip affixed, in FIG. 5A, to the wall opposite the connection arrangement and, in FIG. 5B, to the same wall as the connection arrangement.
Figure 5B:
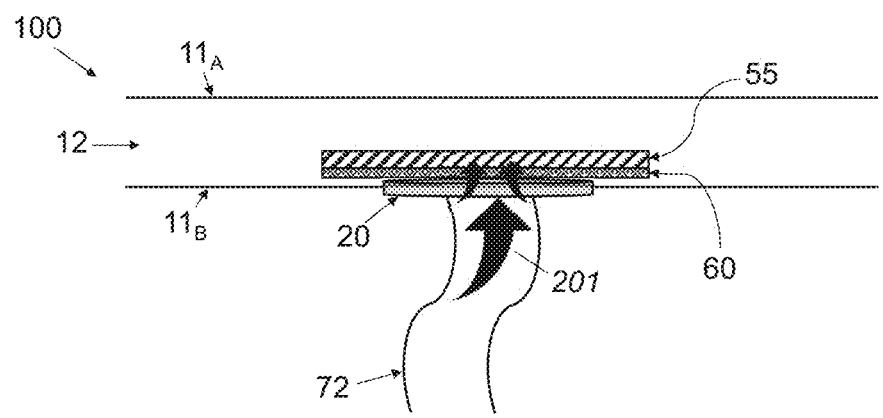

FIGS. 5A and 5B show a detail of an apparatus 100 illustrating the flow of a gas into and out of a bag 10, through a connection arrangement 20. In FIG. 5A, the connecting arrangement 20 is mounted to a wall 11B of a bag 10, and a strip 50 is affixed to a second wall $11_A$, which is 'opposite' the first wall $11_B$, i.e., separated therefrom by the interior volume 12 of the bag 10. The interior volume 12 may not be an actual volume in an initial state when the apparatus 100 is first produced or first provided, but the apparatus 100 being usable necessarily entails creating an interior volume 12 within the bag 10, e.g., for receiving a limb of a user for a therapy. Thus, in the initial state, the strip 50 and the connecting arrangement 20 of FIG. 5A are on opposite walls $11_A$, $11_B$, but there may not be an interior volume separating them. As shown in the example of FIG. 5A, the bottommost layer 60 is the layer affixed to the wall $11_A$ of the bag 10. The term 'bottommost layer' is thus to be interpreted as meaning the layer closest to the wall of a bag to which it is affixed, and, accordingly, the term 'upper layer is to be interpreted as meaning a layer further from that wall to which the strip is affixed, than the bottommost layer. In the example of FIG. 5A, the connecting arrangement 20 is in direct fluid communication with the upper layer 55 of the strip 50. The flow of gas between a pressure-regulating device (not shown in FIGS. 5A-B) and the interior volume 12 of the bag 10 is indicated by arrow 201. The directionality of arrow 201 in FIGS. 5A and 5B is not indicative of a limitation in direction but merely illustrative, and gas can flow in either direction, i.e., both in and out of the bag 10, depending on whether pressure in the bag 10 is being increased or decreased. In the example of FIG. 5B, the connection arrangement 20 is mounted to the same wall $11_B$ to which the strip 50 is affixed.

In order to establish fluid communication between the connection arrangement 20 and the gas-permeable upper layer 55, bottommost layer 60 is necessarily at least partly open to a gas flow, for example, if bottommost layer 60 comprises a gas-permeable material and/or a porously or non-continuous material.

Figure 6:
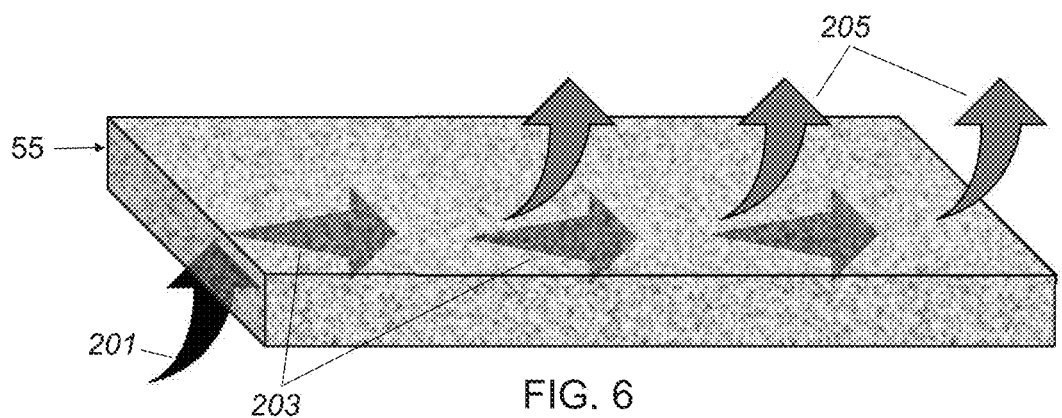
FIGS. 6, 7, 8 and 9A are schematic illustrations of gas-flow pathways into, through and out of strips, according to embodiments of the present invention.

We now refer to FIGS. 6-9, which are respective schematic illustrations of gas-flow pathways in strips 50. All flow arrows 201, 203 and 205 in FIGS. 6-9 are drawn as if illustrating only an inflow of a gas into the bag, but as was the case with FIGS. 5A and 5B, an apparatus 100 is configured so that gas can flow in either direction, i.e., both in and out of the bag 10, depending on whether pressure in the bag 10 is being increased or decreased. FIG. 6 shows a portion of a strip 50 comprising only a gas-permeable upper layer 55 similar to the example of strip $50_4$ shown in FIG. 4F. A gas flow 201 is seen entering the strip from 'below' (i.e., from the direction of a connection arrangement 20 mounted to the same wall 11 that the strip 50 is affixed to (as in the example of FIG. 5B); if the gas-permeable layer 55 is affixed to the wall 11 of the bag 10 with an adhesive or with heat, the affixation is such that a gas flow 201 is still possible through a non-continuous application of adhesive (not shown) or non-continuation heat-welding. The gas flow propagates along the length of the strip (arrows 203) and can 'leave' the strip 50 through an upper surface, i.e., the surface furthest from the wall 11 of the bag 10 to which it is affixed, as indicated by arrows 205. In a use case, a bag 10 is partly evacuated, such that gas in the interior volume 12 of the bag 10 is removed via the connecting arrangement 20, and the two walls 11 of the bag 10 are brought together by the 'negative' pressure. 'Partially evacuated' means that a gas pressure in the bag is reduced to 560 mm Hg, or no more than 560 mm Hg, or to 660 mm Hg, or to no more than 660 mm Hg. The strip 50, being at most partly compressible, maintains a gas-flow pathway from the connection arrangement 20 (e.g., where arrow 201 is shown 'entering' the strip 50), to any point on the upper surface of the strip, e.g., a point at which a pressure-related therapy is direction. As discussed earlier, the gas-flow pathway has no directionality. The term 'maintains a gas-flow pathway' and other similar terms mean remaining open for a gas flow therethrough, wherein the gas flow is adequate for the purposes of the relevant therapy or other purpose. In an illustrative, non-limiting example related to a negative-pressure wound therapy, a bag is partially evacuated to 560 mm Hg absolute gas pressure, all of the air is removed from the bag except for air remaining within the gas-flow pathway, i.e., of a gas-permeable strip or layer or material, and the gas-flow pathway is 'maintained', i.e., there is enough gas flow therethrough to allow for the negative pressure to be transmitted from the connecting arrangement to, for example, a wound in fluid communication with the gas-permeable material.

Figure 7:
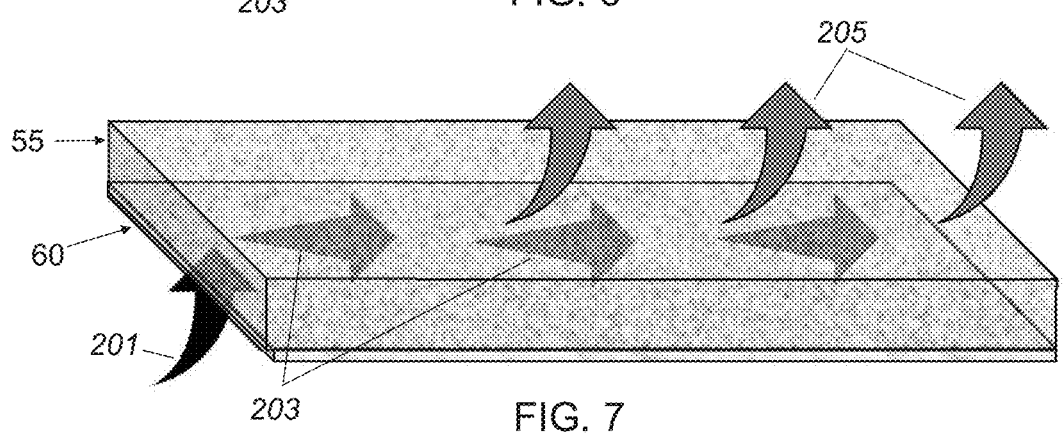
Figure 8:
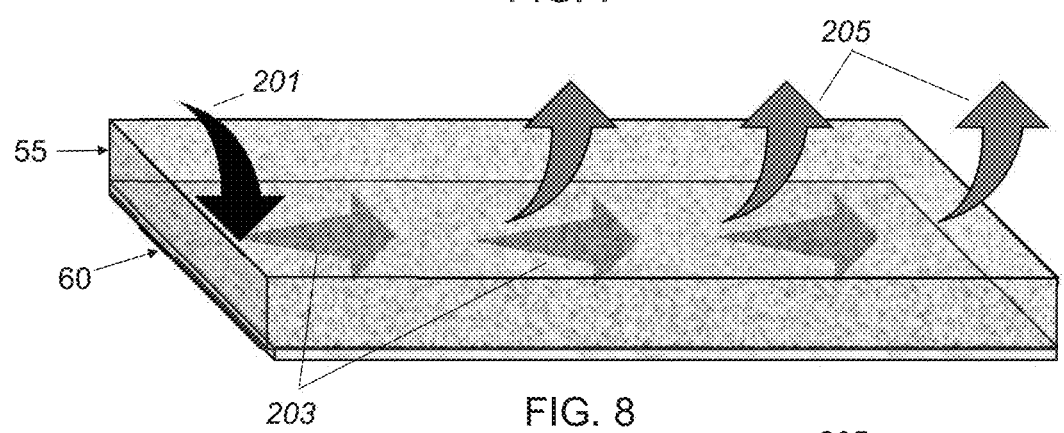

Similarly, FIG. 7 illustrates another strip 50, analogous to the strip 50 of FIG. 5B, wherein the gas-flow pathway passes through (arrow 201) the bottommost layer 60 through, e.g., pores and/or areas of non-continuous application of heat joining or adhesive. In a non-limiting example, the bottommost layer 60 is removed from that area of the strip 50 placed directly over the opening 25 of the connection arrangement 20. FIG. 8 illustrates a gas-flow pathway in another exemplary strip 50, analogous to the strip 50 of FIG. 5A, in which the gas-permeable upper layer 55 is affixed to the wall opposite the wall to which the connection arrangement is mounted, and is thus in direct fluid communication with the connection arrangement 20. The strip 50 of FIG. 9A is analogous to the strip $50_3$ of FIG. 4E, in which an at least partly gas-permeable uppermost layer (or coating) 58 is interposed between the gas-permeable upper layer 55 and the interior 12 of the bag 10.

In all of the examples of FIGS. 6-9A, the apparatus 100 is configured, and component materials are selected, such that a gas-flow pathway can be maintained through the gas-permeable upper layer 55, e.g., the flow-path (in either direction) indicated by arrows 201, 203, 205 within a broad range of pressures relative to pressure-related therapies. An adequate gas-flow pathway is one that is adequate for a flow of gas that is required by the pressure-related therapies. In examples, a pressure-regulating mode of the apparatus 100 can include reaching and/or maintaining a pressure inside the bag 10 within a range of 460 mm Hg to 1060 mm Hg, or within a range of 460 mm Hg (i.e., 300 mm Hg of 'negative pressure) to 760 mm Hg, or within a range of 560 mm Hg to 760 hg, or within a range of 760 mm Hg to 1060 mm Hg (i.e., 300 mm Hg of positive pressure), or within a range of 760 mm Hg to 960 mm Hg. In embodiments, it can be desirable that the material(s) of the gas-permeable upper layer 55 be selected so that the upper layer 55 (and the strip 50 as a whole) is at most partly compressible, i.e., not completely compressible, since being completely compressible could allow the gas-flow pathway to be closed off at one or more points, or even completely, with application of a 'negative' pressure, i.e., evacuation of the bag 10.

Figure 9A:
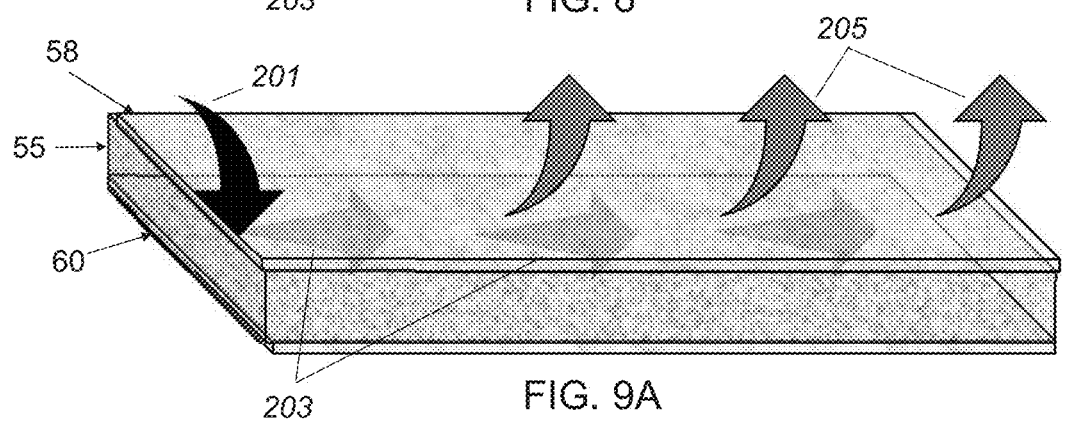
Figure 9B:
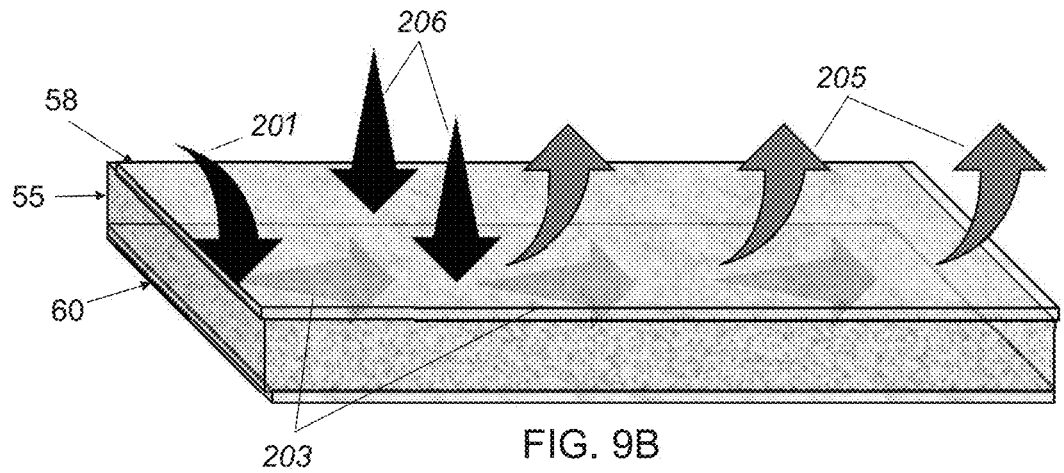
FIG. 9B is a schematic illustrations of gas-flow pathways into, through and out of a strip and with an externally-applied pressure, according to embodiments of the present invention.

FIG. 9B shows the strip 50 of FIG. 9A, with the addition of an externally-applied pressure (indicated in FIG. 9B by arrows 206, e.g., a mechanical pressure, that is applied from outside the bag 10, e.g., to an outer surface of the bag wall $11_B$ of FIG. 5A. Note: with the exception of the externally-applied pressure illustrated in FIG. 9B, all other pressures disclosed herein are gas pressures. Moreover, any pressure cited in this disclosure or in the claims appended thereto that are at least 460 mm Hg is an 'absolute' pressure even if not explicitly described as such, whilst pressures of 100 mm Hg are 'gauge' pressures, even if not explicitly described as such. The pressure is transmitted through the bag wall 11 (not shown in FIG. 9B) to the uppermost layer 58 of the strip, causing compression of the gas-permeable layer 55. In some examples, the compression of the gas-permeable layer 55 due to the application of the externally-applied pressure 206 is in addition to compression caused by, for example, a negative (less than ambient) pressure, i.e., partial evacuation of the bag 10, in a pressure-regulating mode. In the example of FIG. 9B, the apparatus 100 is configured, and component materials are selected, such that a gas-flow pathway can be maintained through the gas-permeable upper layer 55, e.g., the flow-path (in either direction) indicated by arrows 201, 203, 205 within a broad range of externally-applied pressures relative to pressure-related therapies. An adequate gas-flow pathway is one that is adequate for a flow of gas that is required by the pressure-related therapies. In examples, a pressure-regulating mode of the apparatus 100 can include an externally-applied pressure 206 reaching and/or maintaining a pressure transmitted to the gas-permeable layer through bag wall 11 and uppermost layer 58 (if present) in a range from 0 mm Hg to 20 mm Hg, or from 0 mm Hg to 30 mm Hg, or from 0 mm Hg to 40 mm Hg, or from 0 mm Hg to 50 mm Hg, or from 0 mm Hg to 60 mm Hg, or from 0 mm Hg to 70 mm Hg, or from 0 mm Hg to 80 mm Hg, or from 0 mm Hg to 90 mm Hg, or from 0 mm Hg to 100 mm Hg.

Figure 10A:
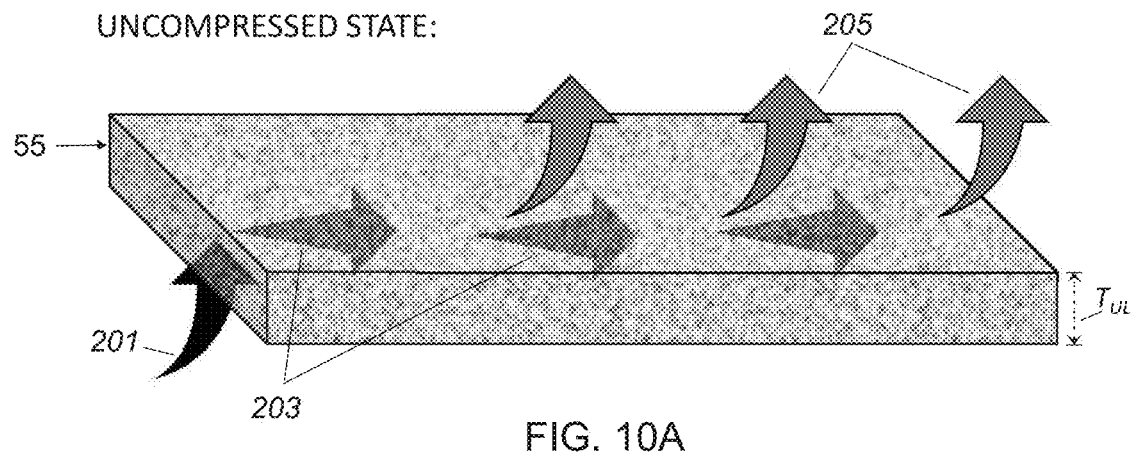
FIGS. 10A and 10B are schematic illustrations of gas-flow pathways into, through and out of a strip in respective uncompressed and partly compressed states, according to embodiments of the present invention.
Figure 10B:
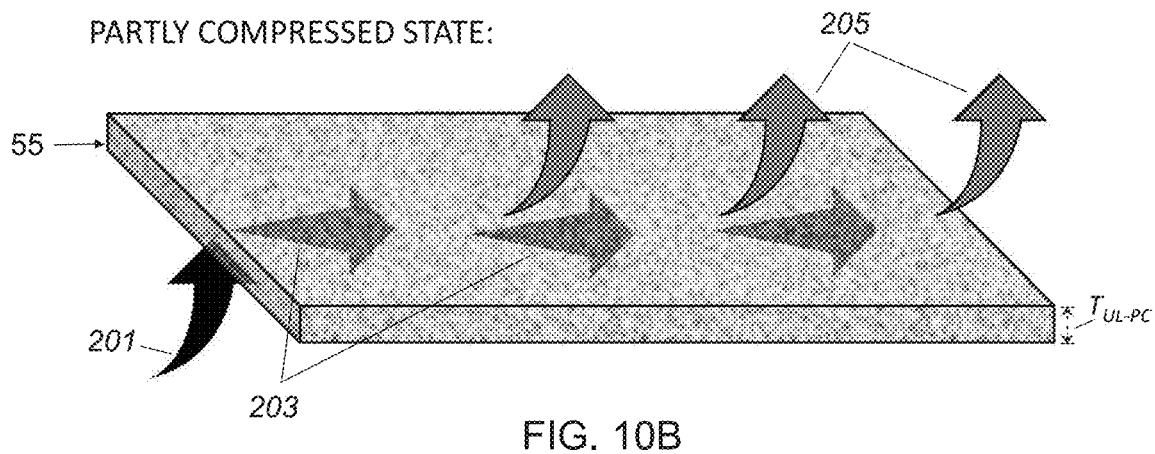

A partly-compressible, gas-permeable upper layer 55 is shown in an uncompressed state in FIG. 10A, and in a partly compressed state in FIG. 10B. The thickness of the upper layer 55 is reduced, by the partial compressing, from $T_{UL}$ to $T_{UL-PC}$ by the force of compression, e.g., from partial evacuation of a bag 10 by a pressure-regulating device, e.g., pressure-regulating device 70 of FIG. 3. The bidirectional gas flows indicated by arrows 201, 203 and 205 continue provide a viable gas-flow pathway in the partially compressed state of FIG. 10B.

We refer now to FIGS. 11A-F, which show photographs of 5 exemplary partially-compressible, gas-permeable upper layers 55 according to embodiments.

Figure 11A:
FIGS. 11A-F show photographs of exemplary gas-permeable strips, and gas-permeable layers of strips, according to embodiments of the present invention.

The partially-compressible, gas-permeable upper layer 55 of FIG. 11A comprises a felt fabric.

Figure 11B:

The partially-compressible, gas-permeable upper layer 55 of FIG. 11B comprises a French terry fabric.

Figure 11C:

The partially-compressible, gas-permeable upper layer 55 of FIG. 11C comprises a nylon loop fabric—the foreground of the photograph also shows a woven fabric base layer, e.g., intermediate later 57 of FIGS. 4B-C.

Figure 11D:

The partially-compressible, gas-permeable upper layer 55 of FIG. 11D comprises a cotton terry fabric.

Figure 11E:
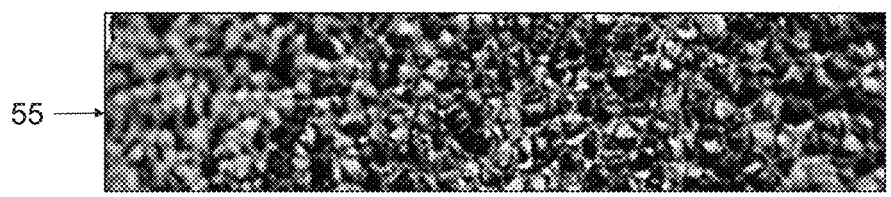

The partially-compressible, gas-permeable upper layer 55 of FIG. 11E comprises a polyurethane foam sheet.

Figure 11F:
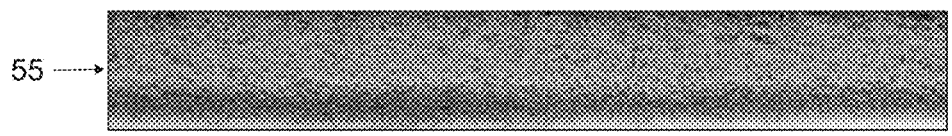

The partially-compressible, gas-permeable upper layer 55 of FIG. 11F comprises a partially compressed mat of non-woven synthetic fibers, e.g., nylon or cellulose.

The foregoing 6 non-limiting examples of suitable materials for gas-permeable upper layers 55 are all capable of maintaining a viable gas-flow pathway when partially compressed, as illustrated in FIG. 10B.

Figure 12:
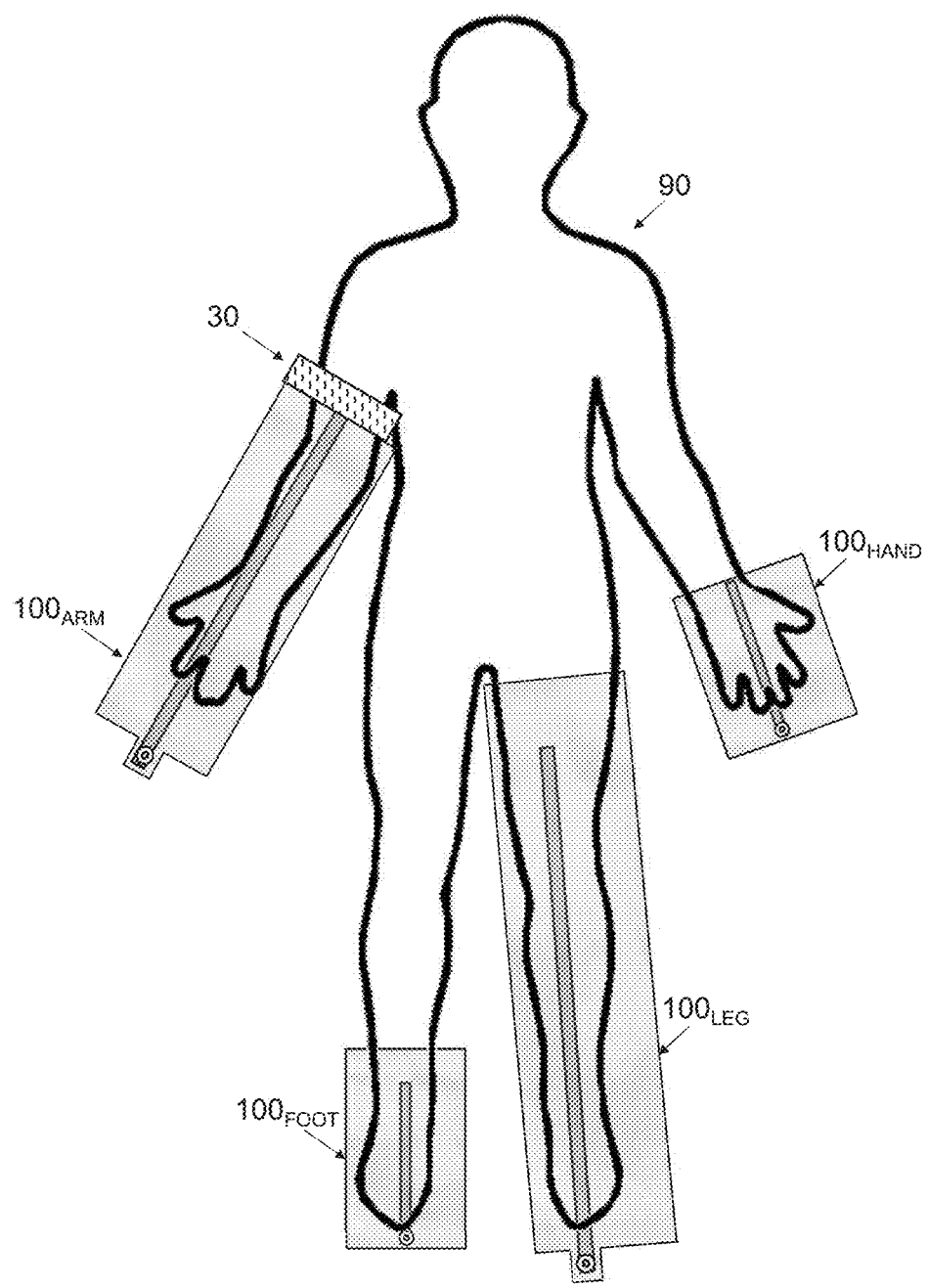
FIG. 12 is a schematic illustration of apparatuses sized for human limbs, in respective donned mode, according to embodiments of the present invention.

In embodiments, it can be desirable to size an apparatus 100 in accordance with a specific type of adult limb. In the schematic illustration of FIG. 12, four examples of limb-sized apparatuses 100 are shown in respective donned modes for 4 limbs of user 90 (clockwise from left): $100_{ARM}$ provided in a size suitable for easy and convenient use of an adult human arm; $100_{HAND}$ provided in a size suitable for easy and convenient use of an adult human hand; $100_{LEG}$ provided in a size suitable for easy and convenient use of an adult human leg; and $100_{FOOT}$ provided in a size suitable for easy and convenient use of an adult human foot. In embodiments, each limb-specific apparatus can be sized to received at least a majority of the specific limb, or most of the limb, or all of the limb up to a joint, e.g., wrist for a hand-apparatus, shoulder for an arm-apparatus, etc. Any of the apparatuses can be provided without a tab-section extension 15 (as shown in the case of $100_{HAND}$ and $100_{FOOT}$) or with a tab-section extension 15 (as shown in the case of $100_{ARM}$ and $100_{LEG}$). In each of the examples, the connection arrangement 20 is preferably disposed so as to not bother the user's limb to cause discomfort. In embodiments, a limb-sealing element 30, e.g., an adhesive tape, can be provided to provide a seal between the limb and the periphery of the open proximal end of the bag 10.

Figure 13:
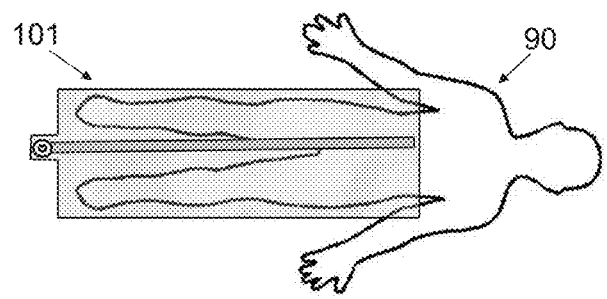
FIGS. 13, 14 and 15 are schematic illustrations of human users with exemplary body-sized apparatuses, according to embodiments of the present invention.
Figure 14:
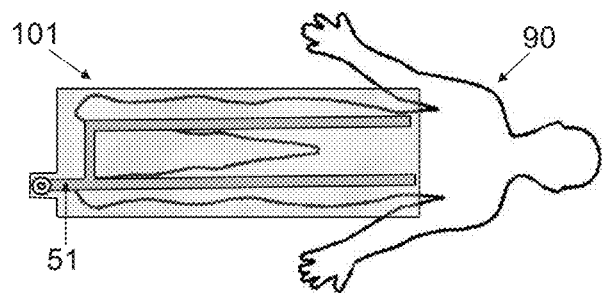
Figure 15:
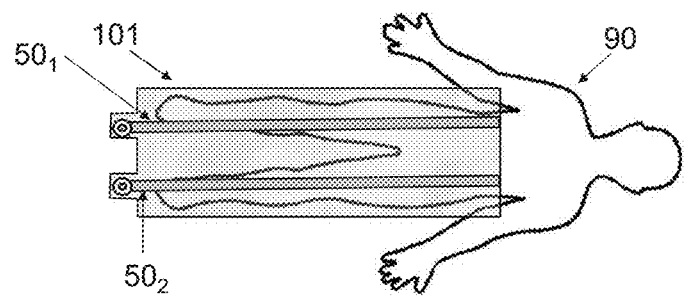

FIGS. 13, 14 and 15 show non-limiting examples of apparatuses 100 intended to for use with a user's torso, or with at least two limbs, e.g., both legs, or with part of a torso including the at least two limbs. FIG. 13 shows an apparatus 100 comprising a single and simple strip 50 and a single connecting arrangement. FIG. 14 shows an alternative configuration for an apparatus 100 including a single, but complex strip 50, where a single connecting arrangement 20 is made to be in fluid communication with two branches of the strip 50. FIG. 15 shows another alternative configuration for a single apparatus 100 including two separate connection arrangements 20 displaced laterally from each other in the distal portion of the bag 10, and two respective strips 50, each in fluid communication with a corresponding connecting arrangement 20. The skilled artisan will understand that the alternative configurations of FIGS. 14 and 15 are easily translated into ordinary apparatuses 100, i.e., apparatuses sized not for a torso but for individual limbs such as the exemplary apparatuses of FIGS. 1-3 and 12.

Figure 16:
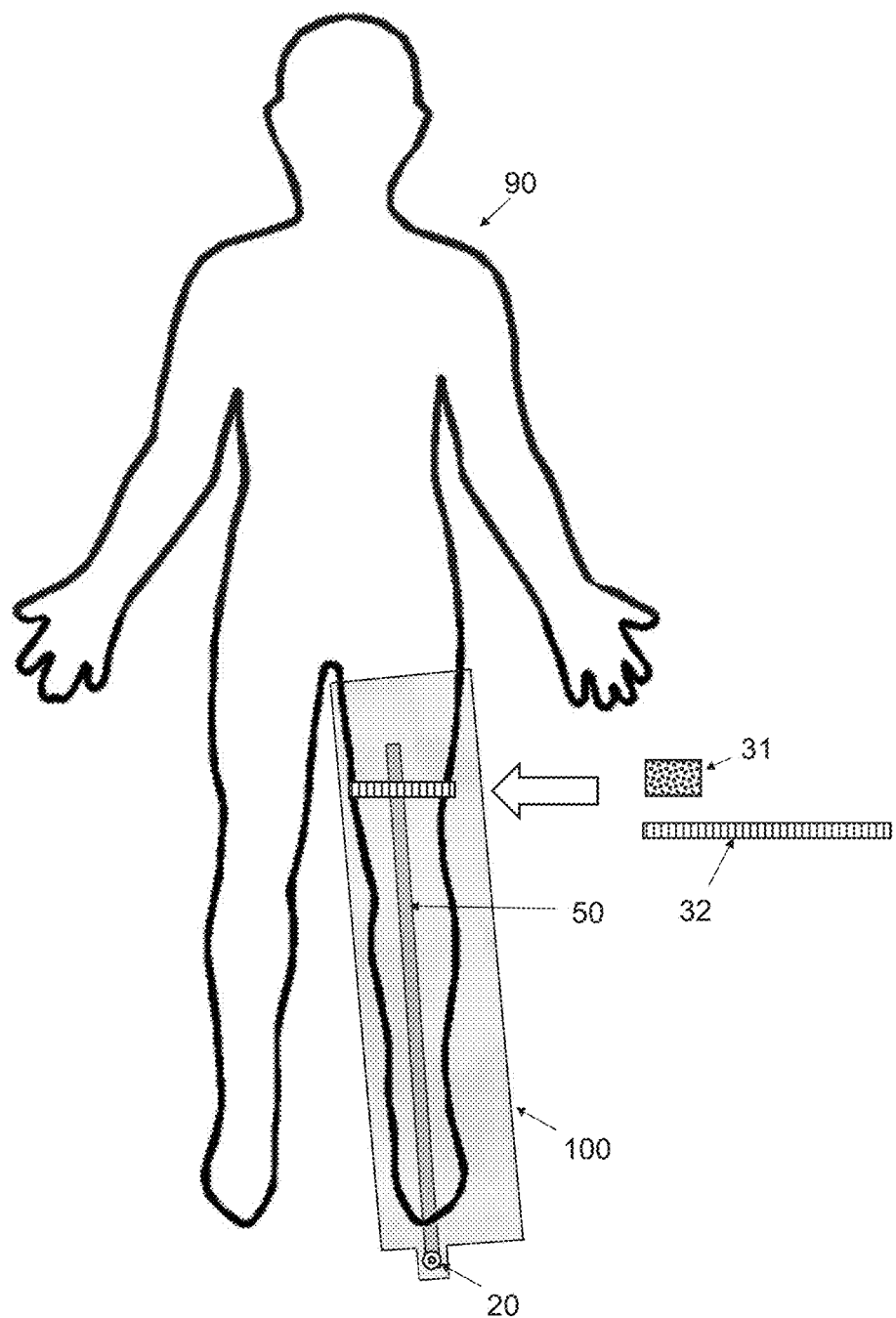
FIG. 16 is a schematic illustration of an apparatus sized for a human leg in a donned mode, together with an elastic ribbon shown in the donned mode as a transverse extension to the strip of the apparatus, according to embodiments of the present invention.

As disclosed hereinabove, a strip 50 is preferably 'soft' enough so as to not provide discomfort to a user. Nonetheless, it can happen that a user is more comfortable not having the strip 50 be in direct contact with a sensitive area, e.g., a wound. Additionally or alternatively, it might be inconvenient in some implementations to line up the connecting arrangement 20 with the user's wound so as to keep the strip in a straight line. Thus, it can be desirable to extend the gas-flow pathway provided by the strip 50 transversely around the circumference of the leg. As illustrated in FIG. 16, an elastic ribbon 32 of a gas-pathway material is provided for disposition, in an on-limb configuration, as a transverse extension of the gas-flow pathway (i.e., extending transversely from the strip, to go around the limb). In some embodiments, a sponge 31 or similarly soft element is provided to be interposed between a wound and the strip 50, or between a wound and the elastic ribbon 32.

Any of the features described herein with respect to the various apparatuses and their respective components can be combined to make new combinations not specifically disclosed herein for purposes of conciseness, and such combinations are well within the scope of the present invention.

Figure 17:
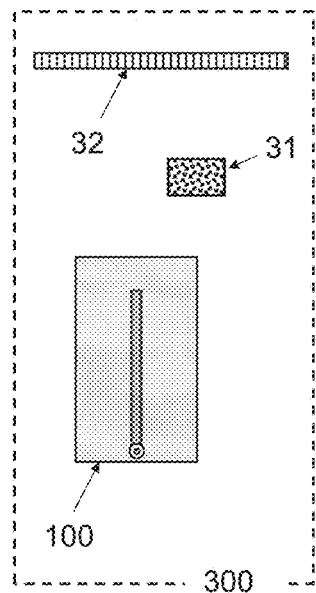
FIG. 17 is a schematic illustration of a kit comprising an apparatus and an elastic ribbon for use as a transverse extension, according to embodiments of the present invention.

FIG. 17 shows a kit comprising an apparatus 100—according to any or more of the embodiments disclosed herein—along with an elastic ribbon 32 and a wound-covering sponge 31.

Figure 18:
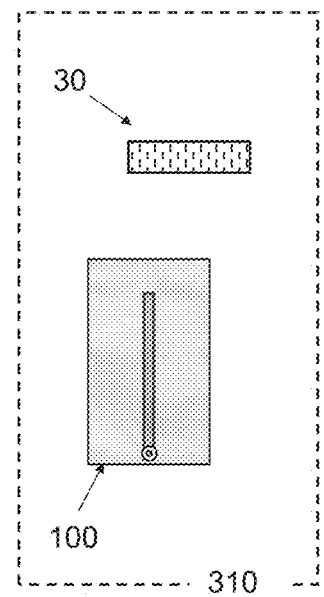
FIG. 18 is a schematic illustration of a kit comprising an apparatus and a limb-sealing tape, according to embodiments of the present invention.

FIG. 18 shows a kit comprising an apparatus 100—according to any or more of the embodiments disclosed herein—along with a limb-sealing tape 30.

Figure 19:
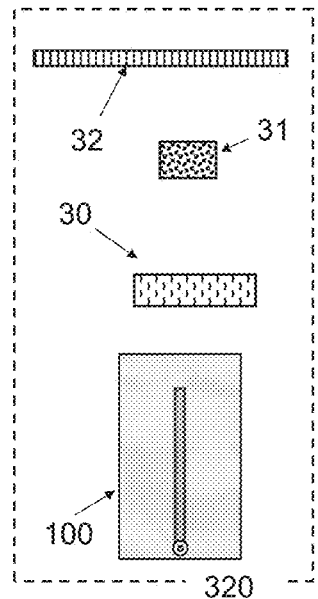
FIG. 19 is a schematic illustration of a kit comprising the elements of the kit of FIG. 17 and a limb-sealing tape, according to embodiments of the present invention.

FIG. 19 shows a kit comprising an apparatus 100—according to any or more of the embodiments disclosed herein—along with an elastic ribbon 32, a wound-covering sponge 31, and a limb-sealing tape 30.

Additional Discussion of the Embodiments

Embodiments of the present invention relate to apparatuses for use with a pressure-regulating device, in applying a therapy to a human limb. According to embodiments, an apparatus for use, with a pressure-regulating device, in applying a therapy to a human limb, comprises: (a) a pliable bag formed to receive, in a donned mode, at least a portion of the limb, through an opening in a proximal portion of the bag; (b) a multilayer strip comprising a bottommost layer affixed to an interior surface of the bag, wherein a distal end of said multilayer strip is disposed in a distal portion of the bag, and wherein a proximal end of said multilayer strip is disposed in said proximal portion of the bag; and (c) a connection arrangement mounted to a wall of the bag in said distal portion thereof, the connection arrangement being effective, in a pressure-regulating mode, to enable therethrough a flow of a gas between the pressure-regulating device and an interior space of the bag, said multilayer strip further comprising an upper layer comprising a partially compressible material defining a gas-flow pathway disposed lengthwise within the bag, between said connection arrangement and said proximal portion of the bag. In some embodiments, said lengthwise gas-flow pathway can be maintained when a gas pressure in the bag is at most 660 mm Hg. In some embodiments, said lengthwise gas-flow pathway can be maintained when a gas pressure inside the bag is 560 mm Hg.

In some embodiments, said lengthwise gas-flow pathway can be maintained when a mechanical pressure of 20 mm Hg gauge is applied externally to the bag and transmitted through a wall of the bag to an uppermost layer of the multilayer strip. In some embodiments, said lengthwise gas-flow pathway can be maintained when a mechanical pressure of 60 mm Hg gauge is applied externally to the bag and transmitted through a wall of the bag to an uppermost layer of the multilayer strip.

In some embodiments, said multilayer strip can have a Shore A hardness of at most 70, or at most 60, or at most 50, or at most 40. In some embodiments, the upper layer of the strip can have a Shore A hardness of at most 70, or at most 60, or at most 50, or at most 40. In some embodiments, it can be that said distal end of said multilayer strip is in fluid communication with said connection arrangement such that said partially compressible material forms a gas-flow pathway from said connection arrangement to said proximal end of said multilayer strip. In some embodiments, said multilayer strip can have a length-to-width ratio of at least 3:1, or of at least 5:1, or at least 10:1. In some embodiments, said multilayer strip can have a length of at least 10 cm, or at least 15 cm, or at least 20 cm, or at least 25 cm, or at least 30 cm. In some embodiments, said multilayer strip can have a thickness of no more than 3.5 mm, or no more than 5 mm, or no more than 7.5 mm, or no more than 10 mm. In some embodiments, said upper layer can have a thickness of no more than 3.5 mm, or no more than 5 mm, or no more than 7.5 mm, or no more than 10 mm.

In some embodiments, the bag can be sized to receive a hand or a foot. In some embodiments, the bag can be sized to receive, lengthwise, at least a majority of an adult human arm. In some embodiments, the bag can be sized to receive, lengthwise, at least a majority of an adult human leg. In some embodiments, said multilayer strip can have a length equal to at least 70% of a length of the bag. In some embodiments, it can be that (i) said distal portion of the bag includes a distally-disposed tab section open to said interior space of the bag, said distal tab section having a width less than 25% of a maximum width of said distal portion of the bag, and/or (ii) said connection arrangement is mounted at least partly within said distally-disposed tab section.

In some embodiments, the therapy can include a negative-pressure wound therapy.

In some embodiments, said pressure-regulating mode can include an interior of the bag being under a vacuum. In some embodiments, said pressure-regulating mode can include a pressure inside the bag within a range of 460 mm Hg to 1060 mm Hg, or within a range of 460 mm Hg to 760 mm Hg, or within a range of 560 mm Hg to 760 hg, or within a range of 760 mm Hg to 1060 mm Hg, or within a range of 760 mm Hg to 960 mm Hg. In some embodiments, said multilayer strip can have a thickness:width dimensionless aspect ratio of between 1:1.5 and 1:20, or between 1:5 and 1:15, or between 1:8 and 1:12.

In some embodiments, said bottommost layer can include an adhesive. In some embodiments, said multilayer strip can be attached to a first wall of the bag and the connection arrangement is mounted to a second wall of the bag. In some embodiments, said multilayer strip can be attached to the same wall that the connection arrangement is mounted to, and/or the bottommost layer of said multilayer strip can be in mechanical contact with the connection arrangement, and/or said upper layer can be in fluid communication with said connection arrangement through said bottommost layer. In some embodiments, the bag can be interiorly pre-sterilized. In some embodiments, the bag can comprise an ozone-resistant material. In some embodiments, said multilayer strip can be effective to maintain fluid communication along a lengthwise path when a portion of said path is subjected to an externally-applied positive pressure of 100 mm Hg.

According to embodiments of the invention, a kit can comprise (i) the apparatus according to any of the embodiments disclosed hereinabove, and/or (ii) an elastic ribbon of a gas-pathway material for disposition, in an on-limb configuration, as a transverse extension of the gas-flow pathway around the limb. In some embodiments, the kit can additionally comprise a sponge for mediating between said partially compressible material and a wound. In some embodiments, the kit can additionally (or alternatively) comprise a limb-sealing tape.

According to embodiments of the invention, an apparatus for use, with a pressure-regulating device, in applying a therapy to a human limb comprises: (a) a pliable bag formed to surround, in a donned mode, at least a portion of the limb; (b) a connection arrangement mounted to a wall of the bag in a distal portion of the bag, the connection arrangement being effective to enable therethrough a flow of a gas between the pressure-regulating device and an interior space of the bag in a pressure-regulating mode; and (c) a gas-permeable strip affixed to an interior surface of the bag and having a length equal to at least 70% of a length of the bag, a distal end of said gas-permeable strip being in communication with said connection arrangement in said distal portion of the bag, and a proximal end of said gas-permeable strip being disposed in a proximal portion of the bag, said gas-permeable strip comprising a partially compressible, gas-permeable material forming a lengthwise gas-flow pathway. In some embodiments, said partially compressible, gas-permeable material can form a lengthwise gas-flow pathway when the bag is at least partly evacuated. In some embodiments, said gas-permeable strip can have a Shore A hardness of at most 70, or at most 60, or at most 50, or at most 40.

In some embodiments, said partially compressible, gas-permeable material can form a gas-flow pathway from said connection arrangement to said proximal end of said gas-permeable strip. In some embodiments, said gas-permeable strip can have a length-to-width ratio of at least 3:1, or of at least 5:1, or at least 10:1. In some embodiments, said gas-permeable strip can have a length of at least 10 cm, or at least 15 cm, or at least 20 cm, or at least 25 cm, or at least 30 cm. In some embodiments, said gas-permeable strip has a thickness of no more than 3.5 mm, or no more than 5 mm, or no more than 7.5 mm, or no more than 10 mm. In some embodiments, the bag can be sized to receive a hand or a foot. In some embodiments, the bag can be sized to receive, lengthwise, at least a majority of an adult human arm. In some embodiments, the bag can be sized to receive, lengthwise, at least a majority of an adult human leg.

In some embodiments, it can be that (i) said distal portion of the bag includes a distally-disposed tab section open to said interior space of the bag, said distal tab section having a width less than 25% of a maximum width of said distal portion of the bag, and/or (ii) said connection arrangement is mounted at least partly within said distally-disposed tab section. In some embodiments, the therapy can include a negative-pressure wound therapy. In some embodiments, said pressure-regulating mode can include an interior of the bag being under a vacuum. In some embodiments, said pressure-regulating mode can includes a pressure inside the bag within a range of 460 mm Hg to 1060 mm Hg, or within a range of 460 mm Hg to 760 mm Hg, or within a range of 560 mm Hg to 760 hg, or within a range of 760 mm Hg to 1060 mm Hg, or within a range of 760 mm Hg to 960 mm Hg.

In some embodiments, said gas-permeable strip can have a thickness:width dimensionless aspect ratio of between 1:1.5 and 1:20, or between 1:5 and 1:15, or between 1:8 and 1:12. In some embodiments, said gas-permeable strip can be attached to a first wall of the bag and said connection arrangement is mounted to a second wall of the bag. In some embodiments, said gas-permeable strip can be attached to the same wall that the connection arrangement is mounted to. In some embodiments, the bag can be interiorly pre-sterilized. In some embodiments, the bag can comprise an ozone-resistant material. In some embodiments, said gas-permeable strip can be effective to maintain fluid communication along a lengthwise path when a portion of said path is subjected to an externally-applied positive pressure of 100 mm Hg.

According to embodiments of the invention, a kit can comprise (i) the apparatus according to any of the embodiments disclosed hereinabove, and/or (ii) an elastic ribbon of a gas-pathway material for disposition, in an on-limb configuration, as a transverse extension of the gas-flow pathway around the limb. In some embodiments, the kit can additionally comprise a sponge for mediating between said partially compressible material and a wound. In some embodiments, the kit can additionally (or alternatively) comprise a limb-sealing tape.

According to embodiments of the invention, an apparatus for use, with a pressure-regulating device, in applying a therapy to a human limb, comprises: (a) a pliable bag formed to surround, in a donned mode, at least a portion of the limb; (b) a connection arrangement mounted to a wall of the bag in a distal portion of the bag, the connection arrangement being effective to enable therethrough a flow of a gas between the pressure-regulating device and an interior space of the bag in a pressure-regulating mode; and (c) a gas-permeable strip affixed to an interior surface of the bag, a distal end of said gas-permeable strip being in communication with said connection arrangement in said distal portion of the bag, and a proximal end of said gas-permeable strip being disposed in a proximal portion of the bag, said gas-permeable strip comprising a partially compressible, gas-permeable material forming a lengthwise gas-flow pathway, wherein said gas-permeable strip has a thickness:width dimensionless aspect ratio of between 1:5 and 1:15.

In some embodiments, said lengthwise gas-flow pathway can be maintained when a gas pressure in the bag is at most 660 mm Hg. In some embodiments, said lengthwise gas-flow pathway can be maintained when a gas pressure inside the bag is 560 mm Hg.

In some embodiments, said lengthwise gas-flow pathway can be maintained when a mechanical pressure of 20 mm Hg gauge is applied externally to the bag and transmitted through a wall of the bag to an uppermost layer of the multilayer strip. In some embodiments, said lengthwise gas-flow pathway can be maintained when a mechanical pressure of 60 mm Hg gauge is applied externally to the bag and transmitted through a wall of the bag to an uppermost layer of the multilayer strip. In some embodiments, said gas-permeable strip can have a Shore A hardness of at most 70, or at most 60, or at most 50, or at most 40. In some embodiments, said partially compressible, gas-permeable material can form a gas-flow pathway from said connection arrangement to said proximal end of said gas-permeable strip. In some embodiments, said gas-permeable strip can have a length-to-width ratio of at least 3:1, or of at least 5:1, or at least 10:1. In some embodiments, said gas-permeable strip can have a length of at least 10 cm, or at least 15 cm, or at least 20 cm, or at least 25 cm, or at least 30 cm. In some embodiments, said gas-permeable strip can have a thickness of no more than 3.5 mm, or no more than 5 mm, or no more than 7.5 mm, or no more than 10 mm.

In some embodiments, the bag can be sized to receive a hand or a foot. In some embodiments, the bag can be sized to receive, lengthwise, at least a majority of an adult human arm. In some embodiments, the bag can be sized to receive, lengthwise, at least a majority of an adult human leg. In some embodiments, it can be that (i) said distal portion of the bag includes a distally-disposed tab section open to said interior space of the bag, said distal tab section having a width less than 25% of a maximum width of said distal portion of the bag, and/or (ii) said connection arrangement is mounted at least partly within said distally-disposed tab section. In some embodiments, the therapy can include a negative-pressure wound therapy. In some embodiments, said pressure-regulating mode can include an interior of the bag being under a vacuum. In some embodiments, said pressure-regulating mode can include a pressure inside the bag within a range of 460 mm Hg to 1060 mm Hg, or within a range of 460 mm Hg to 760 mm Hg, or within a range of 560 mm Hg to 760 hg, or within a range of 760 mm Hg to 1060 mm Hg, or within a range of 760 mm Hg to 960 mm Hg.

In some embodiments, said gas-permeable strip can have a length equal to at least 70% of a length of the bag. In some embodiments, said gas-permeable strip can be attached to a first wall of the bag and said connection arrangement is mounted to a second wall of the bag. In some embodiments, said gas-permeable strip can be attached to the same wall that the connection arrangement is mounted to. In some embodiments, the bag can be interiorly pre-sterilized. In some embodiments, the bag can comprise an ozone-resistant material. In some embodiments, said gas-permeable strip can be effective to maintain fluid communication along a lengthwise path when a portion of said path is subjected to an externally-applied positive pressure of 100 mm Hg.

According to embodiments of the invention, a kit can comprise (i) the apparatus according to any of the embodiments disclosed hereinabove, and/or (ii) an elastic ribbon of a gas-pathway material for disposition, in an on-limb configuration, as a transverse extension of the gas-flow pathway around the limb. In some embodiments, the kit can additionally comprise a sponge for mediating between said partially compressible material and a wound. In some embodiments, the kit can additionally (or alternatively) comprise a limb-sealing tape.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons skilled in the art to which the invention pertains.

The invention claimed is:

1. Apparatus for use, with a pressure-regulating device, in applying a therapy to a human limb, the apparatus comprising:

a) a bag formed and configured to receive, in a donned mode, at least a portion of the limb, through an opening in a proximal portion of the bag;
b) a multilayer strip comprising a bottommost layer affixed to an interior surface of the bag, wherein a distal end of said multilayer strip is disposed in a distal portion of the bag, and wherein a proximal end of said multilayer strip is disposed in said proximal portion of the bag; and
c) a connection arrangement mounted to a wall of the bag in said distal portion thereof, the connection arrangement being effective, in a pressure-regulating mode, to enable therethrough a flow of a gas between the pressure-regulating device and an interior space of the bag,
said multilayer strip further comprising a gas permeable upper layer distinct from said bottommost layer, said upper layer comprising a partially compressible material, said upper layer defining a gas-flow pathway disposed lengthwise within the bag, between said connection arrangement and said proximal portion of the bag, said multilayer strip being laterally open along its length to the interior space of the bag from the distal portion of the bag to the proximal portion of the bag, such that when the bag is in a non-evacuated state, a fluid disposed within the bag flows freely into and out of the partially compressible material of said upper layer.

2. The apparatus of claim 1, wherein said lengthwise gas-flow pathway is maintained when a gas pressure in the bag is at most 660 mm Hg.

3. The apparatus of claim 1, wherein said multilayer strip has a thickness-to-width dimensionless aspect ratio of between 1:2.5 and 1:20.

4. The apparatus of claim 1, wherein said lengthwise gas-flow pathway is maintained when a gas pressure inside the bag is 560 mm Hg.

5. The apparatus of claim 1, wherein said multilayer strip has a Shore A hardness of at most 70.

6. The apparatus of claim 1, wherein said distal end of said multilayer strip is in fluid communication with said connection arrangement such that said partially compressible material forms said gas-flow pathway from said connection arrangement to said proximal end of said multilayer strip.

7. The apparatus of claim 1, wherein said multilayer strip has a length-to-width ratio of at least 3:1.

8. The apparatus of claim 1, wherein said multilayer strip has a length of at least 10 cm.

9. The apparatus of claim 1, wherein said multilayer strip has a thickness of no more than 5 mm.

10. The apparatus of claim 1, wherein said upper layer has a thickness of no more than 3.5 mm.

11. The apparatus of claim 1, wherein the bag is configured to be sized to receive a hand or a foot.

12. The apparatus of claim 1, wherein said multilayer strip has a length equal to at least 70% of a length of the bag.

13. The apparatus of claim 1, wherein (i) said distal portion of the bag includes a distally disposed tab extension open to said interior space of the bag, said distal tab extension having a width less than 25% of a maximum width of said distal portion of the bag, and (ii) said connection arrangement is mounted at least partly within said distally disposed tab extension.

14. The apparatus of claim 1, wherein the bottommost layer includes an adhesive.

15. The apparatus of claim 1 wherein said multilayer strip is attached to a first wall of the bag and the connection arrangement is mounted to a second wall of the bag.

* * * * *